United States Patent
Heydlauf et al.

(10) Patent No.: US 11,334,060 B2
(45) Date of Patent: May 17, 2022

(54) ALERT-ENABLED PASSIVE APPLICATION INTEGRATION

(71) Applicant: Siemens Healthcare Diagnostics Inc., Tarrytown, NY (US)

(72) Inventors: Michael Heydlauf, Cary, NC (US); Shon Ferguson, Raleigh, NC (US); Sara Kendrick, Dallas, TX (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 358 days.

(21) Appl. No.: 16/636,358

(22) PCT Filed: Aug. 24, 2018

(86) PCT No.: PCT/US2018/047845
§ 371 (c)(1),
(2) Date: Feb. 4, 2020

(87) PCT Pub. No.: WO2019/050697
PCT Pub. Date: Mar. 14, 2019

(65) Prior Publication Data
US 2020/0166918 A1    May 28, 2020

Related U.S. Application Data

(60) Provisional application No. 62/554,612, filed on Sep. 6, 2017.

(51) Int. Cl.
*G06F 9/44* (2018.01)
*G06F 11/00* (2006.01)
(Continued)

(52) U.S. Cl.
CPC ......... *G05B 23/027* (2013.01); *G06F 3/0482* (2013.01); *G06Q 10/06* (2013.01); *G16H 10/40* (2018.01); *G16H 40/40* (2018.01)

(58) Field of Classification Search
CPC ...... G05B 23/027; G16H 10/40; G16H 40/40; G06F 3/0482; G06Q 10/06
See application file for complete search history.

(56) References Cited

U.S. PATENT DOCUMENTS 10,811,141 B2 * 10/2020 Hu .................. G16H 10/60
2007/0055545 A1    3/2007 Maughan et al.
(Continued)

FOREIGN PATENT DOCUMENTS

| WO | 2008024471 | 2/2008 |
| WO | 2015187480 | 12/2015 |

OTHER PUBLICATIONS

Zhang et al., Sensor fault detection for industrial systems using a hierarchical clustering-based graphical user interface, 6 pages (Year: 2012).*

(Continued)

*Primary Examiner* — Thuy Dao

(57) ABSTRACT

A software-implemented, alert-enabled passive element and method that allows a user to receive updates from unrelated sources and to provide alerts and status information within a centralized information source without customization or modification of the unrelated sources. Data and information from multiple, independent systems is integrated into a single element that provides a centralized information source. A user is provided with the ability to specify the type of data to be gathered from the independent systems, the specific location where the data is to be retrieved, and a reference value for each instance of data to be retrieved. A comparison between the retrieved data and the reference value is thus enabled. Information regarding a mismatch or retrieved value beyond or outside an acceptable value or range of values may then be provided to the user within the passive element.

28 Claims, 4 Drawing Sheets

(51) Int. Cl.
*G06F 9/445* (2018.01)
*G06F 15/00* (2006.01)
*G05B 23/02* (2006.01)
*G16H 10/40* (2018.01)
*G16H 40/40* (2018.01)
*G06F 3/0482* (2013.01)
*G06Q 10/06* (2012.01)

(56) References Cited

U.S. PATENT DOCUMENTS

2007/0282997 A1  12/2007  Trochman
2009/0271726 A1  10/2009  Gavimath et al.
2011/0013447 A1   1/2011  Hanzawa et al.
2011/0170667 A1   7/2011  Ruggiero et al.
2013/0207812 A1   8/2013  Heydlauf
2014/0372809 A1  12/2014  Du et al.
2015/0260713 A1   9/2015  Ghaffari et al.

OTHER PUBLICATIONS

International Search Report for PCT/US2018/047845 dated Oct. 29, 2018.

* cited by examiner

70

Configure Group

| | |
|---|---|
| Group Name | sLIM |
| Base URL | http://487.19.48.8 |
| Alert Tile | sLIM ▼ |
| Fetch Interval | 5    minutes ▼ |

Fig. 4

ALERT-ENABLED PASSIVE APPLICATION INTEGRATION

CROSS-REFERENCE TO RELATED APPLICATIONS

This patent application claims priority of U.S. Pat. Appl. No. 62/554,612, filed Sep. 6, 2017, the disclosure of which is hereby incorporated in its entirety by reference.

FIELD OF THE DISCLOSURE

The disclosure herein relates generally to the field of a system and method for providing an interactive user-interface for monitoring the status of data, display objects, or conditions associated with other, independent systems and applications and for selectively reporting the status thereof to a user and for selectively assigning one of a plurality of degrees of importance to the respective status.

BACKGROUND

In the modern diagnostics laboratory, lab professionals are required to interact with and react to many disparate instruments, each running different software systems. Their attention is split monitoring multiple different elements including a Laboratory Information System (LIS), middleware, and instruments in order to ensure that the necessary medical and other tests are being performed optimally and without error. In such a high-throughput environment, real-time feedback is critical and it is crucial that any problems that arise are dealt with as swiftly as possible.

Methods of integrating information from these vital systems into a single source, whereby a lab professional may monitor multiple inputs at once, are very valuable. Having a single, central application that integrates with the other systems of interest is useful not only because it reduces the unnecessary effort of the lab professional and increases the efficiency of the laboratory, but also because it reduces the risk of medical error by identifying alerts of interest to the lab professional quickly. As every lab and lab worker's needs are different, customizable solutions, where only relevant and important feedback will be provided, are essential.

However, prior approaches to providing centralized collection and dissemination of status information with respect to distributed processes have relied upon tight integration of disparate software and firmware applications. Initial configuration of such a tightly bound system requires a significant degree of expertise in each of the integrated processes. Further, replacement, upgrade, or addition of any one process into the integrated system requires time, effort, and expertise. A risk of interfering with the proper functioning of such an integrated process is introduced through the requirement of interactive, customized data exchange.

It is thus desirable to provide a form of virtual integration of disparate information sources, in laboratory and other environments, without requiring any development or changes in the integrated systems themselves.

SUMMARY

In order to overcome the inability of the prior art to integrate information from disparate information sources within an environment without requiring changes or customization to those information sources and data storage associated therewith, the present disclosure provides a software-implemented, alert-enabled passive element and method that allows, for example, a laboratory professional to receive updates and alerts from unrelated sources within a centralized information source.

The foregoing system enables the gathering of data and information from multiple, independent systems into a single element that provides a centralized information source. A user is provided with the ability to specify the type of data to be gathered, as well as the specific location where the data is to be retrieved, which may be for example with respect to a page of networked information maintained by such a system, a visual display of data maintained by such a system, or a location in memory or a database associated with such a system. Importantly, no customization of any of the integrated independent systems is required.

In addition, the user is provided with the ability to define a reference value for each instance of data to be retrieved. It is understood that the reference value may be plural values or a range of values. A comparison between the retrieved data and the reference value is thus enabled. Should the comparison reveal a mismatch or retrieved value beyond or outside an acceptable value or range of values, also referred to as an aberrant comparison result, an alert may then be provided to the user within the single element, such as a laboratory wide status display of the centralized information source. The alert may include the retrieved data as well as the respective reference value. The retrieved data value may be updated each subsequent retrieval cycle, which may be at a standard time period or which may be customizable. A user is thus provided with a real-time view of an aspect of the respective independent system.

If conditions associated with an independent system change whereby the comparison of retrieved data and a reference value is a match, also referred to as a positive comparison result, the related alert may be automatically removed from the centralized information source. If the user does not deem the alert to be of significance, either in absolute terms or with respect to other alerts, the user may manually dismiss or inhibit the respective alert through interaction with the centralized information source. Such interaction may be through a touch-sensitive display, mouse, keyboard, or other known human interface devices. The user is also provided with the ability to customize the alert according to the importance of the retrieved data value to the respective independent system or to the overall environment workflow, the degree of variance of the retrieved data from the respective reference value, or the needs or desires of the respective user, among other bases.

In addition, rules of rules may be defined, such that when two or more aberrant results are obtained, the urgency of each may be increased or an additional macro-level alert may be defined. Thus, for example, if there is an indication that a water level is low in two or more independent systems, a macro alert indicating there may be a loss of water to the environment may be generated. Alert urgency may be custom-defined by the user and may include the location of a pop-up window within the centralized information source, the size of the pop-up window, the color, the brightness, or some other visual characteristic. In certain embodiments, the centralized information source may be customizable by a user to provide auditory alerts under certain predefined conditions.

In addition to providing the ability to customize the response of the alert-enabled passive element, the presently disclosed system and method may be preprogrammed with standard response characteristics that are subsequently customizable by a user.

BRIEF DESCRIPTION OF THE DRAWINGS

Illustrative embodiments of the disclosed technology are described in detail below with reference to the attached drawing figures, which are incorporated by reference herein and wherein:

FIG. 4 is an exemplary screenshot of a configuration tool used to customize data retrieval from an independent system integrated by the alert-enabled passive element of the present invention.

DETAILED DESCRIPTION

Disclosed herein is an alert-enabled, passive, interactive user interface element, implemented by a computing device, for integrating data from disparate information sources within an environment through provision of a centralized information source that allows a user to receive alerts and current data from the information sources. Rather than requiring a user to refer to each of the plural, disparate and independent information sources on a periodic basis to obtain or monitor important information regarding the respective system activity within the environment, data from the information sources is periodically retrieved by the passive element and is compared to a respective threshold value or values. Alerts associated with the data retrieved from the plural independent systems may thus be selectively provided to a user via a single user interface without requiring any customization of the independent systems themselves.

Figure 1:
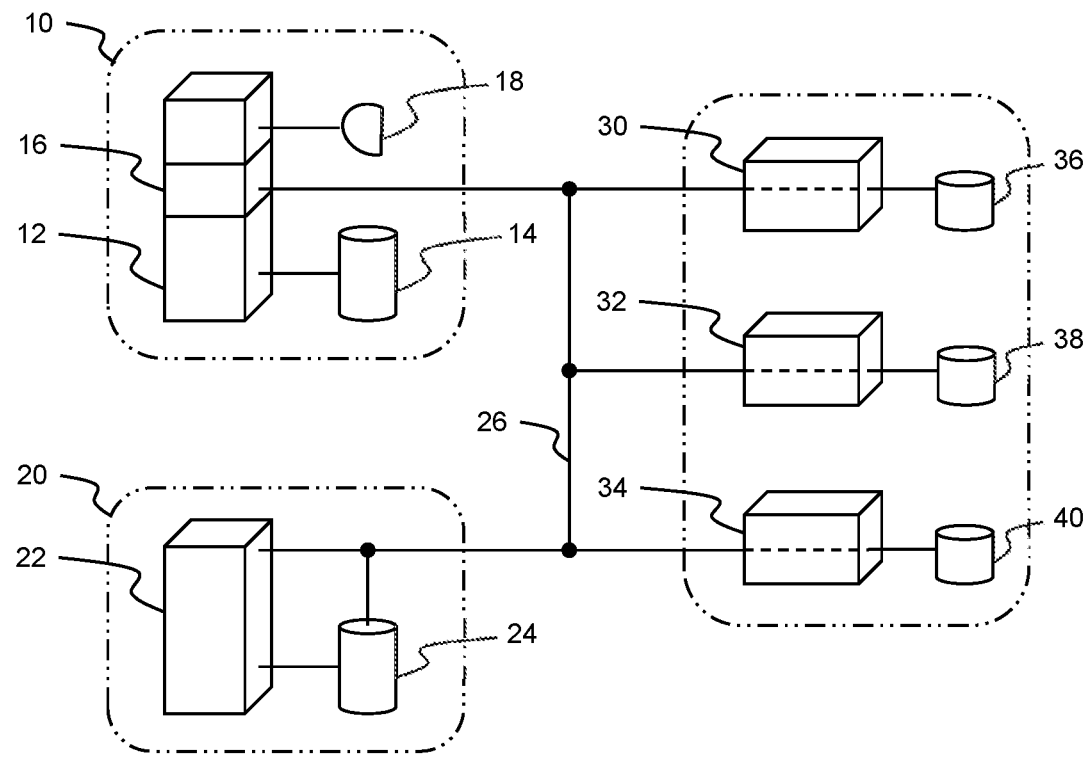
FIG. 1 is schematic block diagram of a system for implementing an alert-enabled passive element according to the present invention along with plural independent systems to which it interfaces.

The presently disclosed system may be embodied within a computing device 10 such as a custom-programmed general purpose personal computer or laptop. For example, FIG. 1 provides a computing device having a processor 12 in communication with a data storage device such as a memory 14. A communications interface 16 of the computing device enables the processor to interact with data associated with other devices 30, 32, 34, as discussed below. A display device 18 is also associated with the computing device. The alert-enabled passive element is provided to a user via the display device.

The computing device 10 implementing the alert-enabled passive element may be in communication with a computing device 20 implementing a Laboratory Information System (LIS) having a processor 22 and associated data storage 24. The alert-enabled passive element computing device 10 may provide information to the LIS, including the user interface itself, the data retrieved from individual, independent devices 30, 32, 34 or data storage devices 36, 38, 40 associated therewith, or the alert conditions determined according to the comparison of retrieved data to reference values stored in the processor memory 14, as discussed subsequently. In another embodiment, the computing device implementing the alert-enabled passive element and the computing device implementing the LIS may be the same device.

Communications between computing devices may be through wired connections, wireless connections via a variety of known modalities, etc.

The alert-enabled passive element computing device 10 is in communication with at least one independent device 30, 32, 34, also referred to as disparate devices as each may be functionally isolated from and independent of the other such devices. In a diagnostics laboratory context, these independent devices may be instruments such as automated blood analyzers with associated sample transport systems. High throughput in a laboratory having plural such instruments thus involves multiple fluidic systems, environmental control systems, transport systems, etc. The complexity of such an environment underscores the need for the presently disclosed ability to integrate data from such disparate systems into a common user interface, but importantly without the need to customize or otherwise alter the data configuration or operation of the constituent systems. Each device has data storage capabilities 36, 38, 40. Such storage may take the form of databases, web pages having links to data stored in databases, etc.

Figure 2:
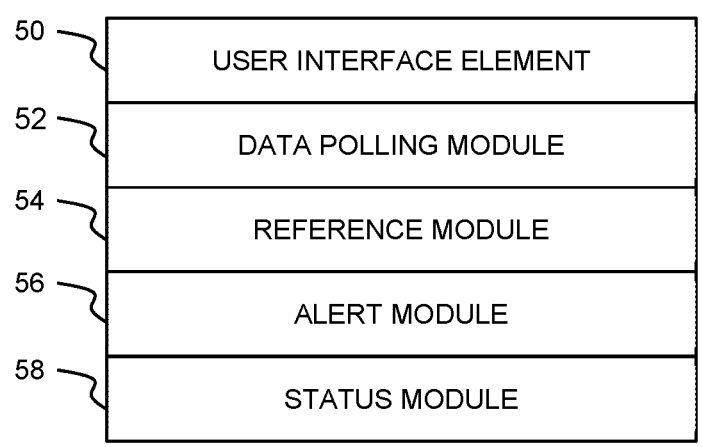
FIG. 2 is a block diagram of functional elements implemented by the system of FIG. 1.

Functional elements and modules implemented by the alert-enabled passive element computing device 10 are depicted in block form in FIG. 2. These include the user interface element 50 which provides the alert-enabled passive element implementing the centralized information source and interactive user interface itself, a data polling module 52 for enabling the retrieval of desired data from storage 36, 38, 40 associated with the independent devices 30, 32, 34 within the respective environment, a reference module 54 for comparing the retrieved data to a reference value stored within the respective data storage device 14, an alert module 56 for selectively generating and managing alerts within the passive element on the basis of the comparison performed by the reference module, and a status module 58 for gathering operational data from each of the independent devices and for selectively providing the information within the passive element for providing enhanced operational awareness of equipment and processes within the respective environment to a user.

Via the display device 18 of the alert-enabled passive element computing device 10, a user is provided with the ability to define, with respect to the independent devices 30, 32, 34, what type of data is to be retrieved, where to retrieve it from, what parameter type is to be used as the reference value, values, or values ranges, and what are the reference value, values, or ranges of values. These functions are part of the reference module 54. For example, the reference module may be used to create a rule for interrogating a value associated with the reagent inventory in a web-based inventory tracking application and for comparing the retrieved data value to a user- or pre-defined threshold value.

Figure 3:
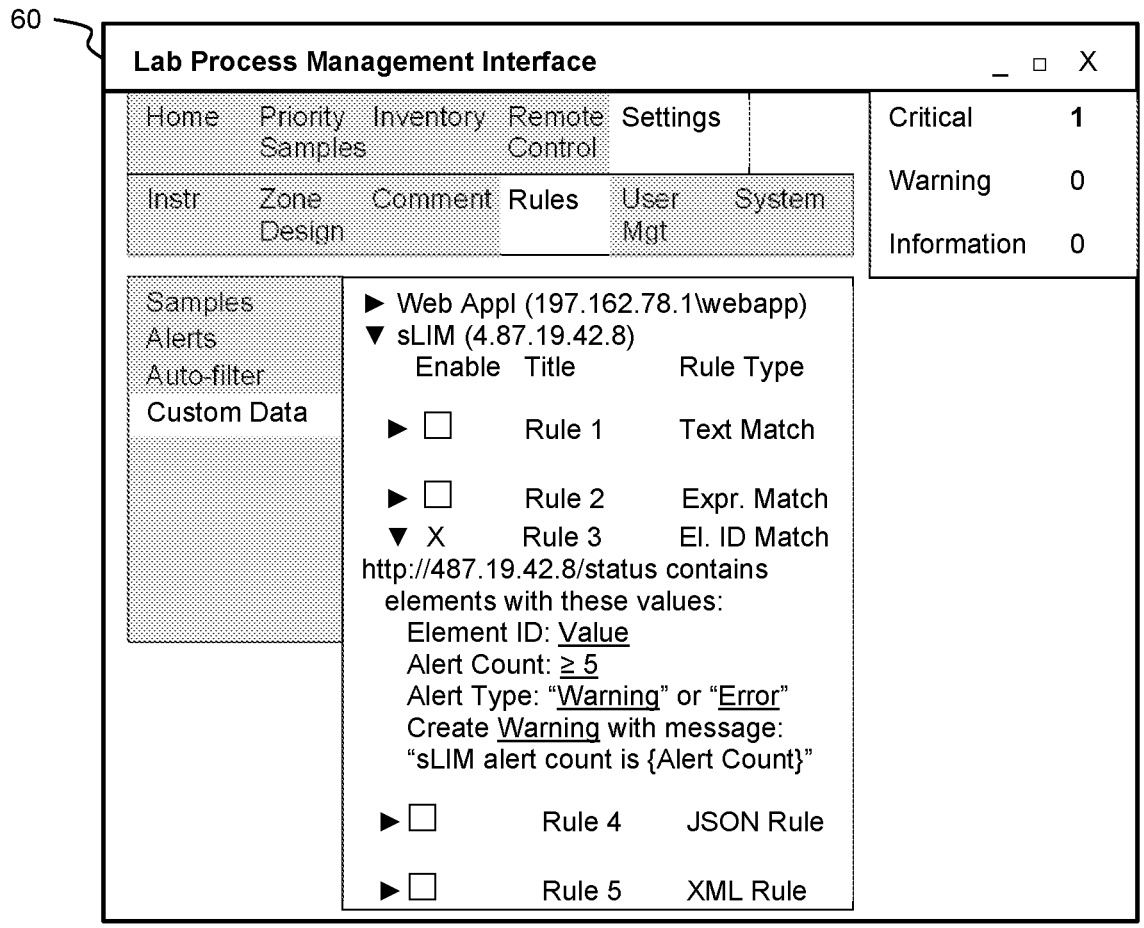
FIG. 3 is an exemplary screenshot of the alert-enabled passive element implemented by the system of FIG. 1 providing customizability of a centralized information source, according to the present invention.

In FIG. 3, an example of an interactive user interface 60 provided on the display device 18, implemented by the respective processor 12, is shown. Here, a user is provided with a variety of top level menu selections. In the illustrated case, the "Settings" tab has been selected. Among the submenu options, the user has selected "Rules." In the illustrated example, a further submenu selection has been made by choosing "Custom Data."

In the illustrated interface, the user is provided with the option of defining data to be retrieved from a web application (Web Appl) having a network address of 197.162.78.1.

However, the user has opted to define data to be retrieved with respect to a SYNGO (Siemens Aktiengesellschaft) brand Laboratory Information Manager (sLIM). Options are presented for selecting one of five types of rules, including: Text Match; Expression Match (Expr. Match); Element ID Match (El. ID Match); JavaScript Object Notation (JSON) Rule; and an Extensible Markup Language (XML) Rule. Other rule types may be employed. Each such rule is provided with definitions for where to find the item to be matched, and other characteristics that define what are acceptable or unacceptable values and how the module should respond if unacceptable values are retrieved.

In the example depicted in FIG. 3, a user has placed an X next to Rule 3, Element ID Match. The elements to be retrieved are identified by the user as being at network address 487.19.42.8 on a page named "status." Note that this address may be preconfigured in certain embodiments or may be entered by the user or user representative based upon the known installation and configuration of the independent devices 30, 32, 34.

Next, a user selects the element ID associated with the value to be retrieved. In this case, the user has selected "Value." The combination of network address, web page, and element ID provide the information necessary for the processor 12, via the communications interface 16, to access the desired data for retrieval. An Alert Count value associated with the identified Element ID is then defined—in this case, an Alert Count "≥5".

Now, the user defines the response of the passive element to a data value agreeing with the Alert Count criteria. In the illustrated example, the Alert Type is set to either "Warning" or "Error." Multiple Alert Types may be definable in case the passive element is configured to respond to only one of the two options selected.

Lastly, in this example, the user has the ability to define how the passive element is to respond to the identified Element ID meeting the Alert Count criteria. In FIG. 3, the user has instructed the passive element to create a Warning message with the text string: "sLIM alert count is" followed by the retrieved Element ID value. Warning, in this example, may be a predefined type of pop-up window or other graphic message conveyed to the user via the passive element user interface.

Similar criteria may be defined for other Rule Types. For example, with respect to Rule Type "Text Match," a user may define a text string such as "Warning," "Low," or "Error," with the appropriate Alert Type and create mandate associated therewith.

In FIG. 4, an example of a Configure Group menu 70, provided by the reference module 54 on the interactive user-interface, is shown. Through such a configuration window, the user is able to associate location data with particular groups of interest. In the illustrated case, rules associated with the sLIM are assigned to the base network address 487.19.48.8. This address thus forms part of a data pointer for individual data elements associated with the sLIM.

Pop-up windows for warnings or alerts associated with the sLIM take the form of a sLIM Alert Tile. This type of Alert Tile may be preconfigured or may be customizable by the user through other setup options associated with the passive element. The user is further able to define how often data associated with the sLIM group is to be retrieved. Regular data retrieval enables the automatic removal of an alert when the underlying condition has been addressed or resolved through a positive comparison by the reference module 54. For example, if an alert window is generated as a result of a reagent level being too low, the alert will be automatically cleared if an operator refills the respective resource and the system next implements the respective rule according to the time interval defined in the respective group configuration.

Figure 5:
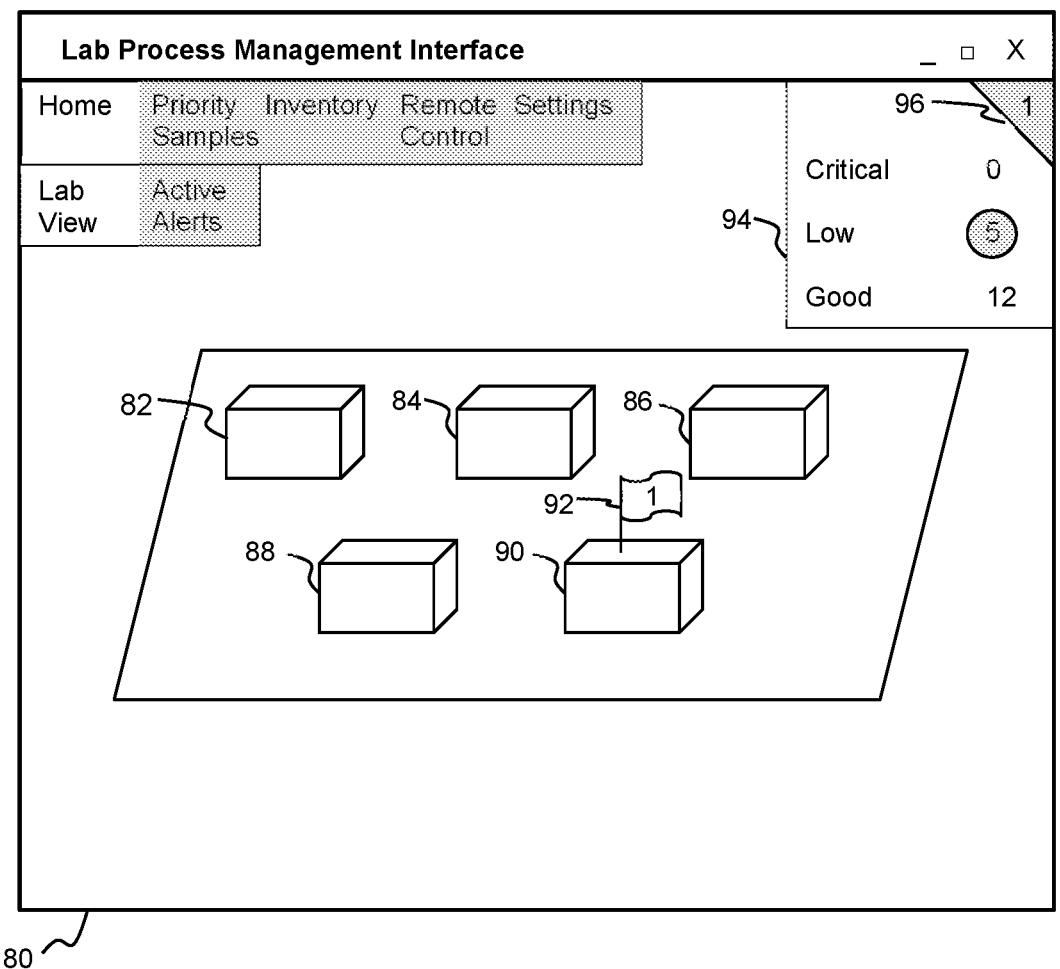
FIG. 5 is an exemplary screenshot of the alert-enabled passive element implemented by the system of FIG. 1 providing information regarding multiple independent systems within an environment, including an alert associated with one of the independent systems.

FIG. 5 represents an exemplary screenshot 80 of the interactive user interface provided by the alert-enabled passive element computing device 10 on the associated display 14. As an aside, the display 14 may be a traditional display that is wired or integrated into the associated processor 12 or may be a display of a device that is available to the laboratory user, such as of a smartphone, tablet computer, or laptop, that is in wired or wireless communication with the processor.

A user has selected a Home option from a main menu bar, and has also selected a Lab View option from a submenu bar. A depiction of instruments 82, 84, 86, 88, 90 within the environment is displayed. These instruments may correspond to the individual independent devices 30, 32, 34 of FIG. 1 and are in communication with the processor 12 implementing the alert-enabled passive element. The depiction may be a simplified graphical rendering, as shown in FIG. 5, or may be a view of the environment as generated by an optical device such as a still or video camera having at least a portion of the environment within a respective field of view. Additional graphical elements are selectively overlaid onto the depiction by the alert module 56 based upon the comparison of retrieved data to a respective reference value(s), performed by the reference module 54.

In the example of FIG. 5, an alert flag 92 associated with the lower right instrument 90 is provided. In addition, within a general environment status window 94 projected within the user interface, the collective status for plural instruments is provided, enabling the user to have insight into the status of plural, independent, discrete instruments at the same time, without the requirement for explicit integration with the processor 12 implementing the passive element. A retrieved "low" data indication has been previously configured to provide an alert condition, represented by the flag 92 visually associated with the lower right instrument 90, and represented by an environment-wide alert indication 96. The former enables a user to rapidly associate an aberrant condition with a physical instrument, while the latter enables a user to rapidly detect the presence of an aberrant condition somewhere within the environment. Real-time feedback is thus enabled.

As discussed above, the retrieved data may be, in addition to a specific numerical value, word, or phrase, data the describes a graphical image, or a digital rendering of a graphical image. For example, with respect to traditional rich-client or non-communicative applications, an integrated application running in the background may be "captured" such as through a screenshot taken at regular temporal intervals. The reference module 54, using image recognition with respect to predefined image standards, may then compare the retrieved image against the predefined standard image, or alternatively against a predefined error image. The standard or error images may be disposed within a database stored, for example, within the memory 14 of the computing device 10 implementing the alert-enabled, passive, interactive user interface. If the reference module is used to compare retrieved image data against error images, an alert state image database, in memory 14, may be built up over time by the user, such as after the user has seen an image of interest and has defined it as an alert state image. Thus the passive element interface may be trained over time by the user to recognize an image as an alert when there is a match with the same or similar retrieved image data.

An example of a computing device 10 is described in the following. The computing device 10 has a processor 12, a memory 14, and I/O or communications interface or circuitry 16 suitably interconnected via one or more communications buses. The computing device 10 is connected to a source of power (which may include an internal battery) (not shown), and may further be connected to a back-up power supply device to prevent failure in the event of power outages. The system memory 14 may include random access memory (RAM) and storage memory. The storage memory may include hard disk drives for reading from and writing to a hard disk, a magnetic disk drive for reading from or writing to a removable magnetic disk, and an optical disk drive for reading from or writing to a removable optical disk, such as a CD, DVD, or other optical media. The storage memory and their associated computer-readable media provide non-volatile storage of computer readable instructions, data structures, program modules, and other data for the computing device 10. Other types of computer readable media which can store data that is accessible by a computer, such as flash memory cards, DVD-ROM, DVD-RAM, and the like, may also be used in the exemplary computing system.

The memory 14 stores an operating system for controlling the operation of the computing device 10. In one embodiment of the disclosure, the operating system provides a graphical operating environment, such as Microsoft Corporation's WINDOWS, LINUX, or Apple's SNOW LEOPARD graphical operating system in which activated applications, programs, or modules are represented as one or more graphical application windows with an interface visible to the user, such as a graphical user interface (GUI). The memory 14 also stores a number of program modules, including the user interface element 50, data polling module 52, reference module 54, alert module 56, and status module 58. As noted, the computing device implementing the passive element interface may be a standalone computing device or may be integrated into another environment-specific computing device such as the one implementing the LIS 20.

As shown in FIG. 1, the computing device 10 includes a communications interface 16 comprising one or more components for communicating with other devices, e.g., laboratory instruments 30, 32, 34, processors 20 implementing an LIM, consumable management systems, environmental control systems, control panels, cell phones, PDA's, laptop computers, network terminals, general purpose computing devices, desktop computers, etc., over a wired and/or wireless network 26, such as a local area network (LAN) or a wide area network (WAN), such as the Internet. As known to those skilled in the art and others, the computing device implementing the alert-enabled, passive, interactive user interface illustrated in FIG. 1 may be configured to retrieve data over one or more networks and to provide the user interface on a user device in addition to or instead of on the display 18. However, since protocols for network communication, such as TCP/IP, are well known to those skilled in the art, those protocols will not be described here. Additionally or alternatively, the computing device may be equipped with a modem (not shown) for connecting to the Internet through a point to point protocol ("PPP") connection or a SLIP connection as known to those skilled in the art. For accessing the Internet, the memory 14 may further include a web browser module.

The computing device 10 as illustrated includes an output device in the form of a graphical display 18, which may include one or more input devices, such as a keyboard, touch pad, microphone, a pointing device, or the like, for inputting data and commands into the computing device 10. The display 18 and associated user input devices are suitably connected through appropriate interfaces, such as serial ports, parallel ports, or a universal serial bus (USB) of the I/O circuitry. As would be generally understood, other peripherals may also be connected to the processor 12 of the computing device in a similar manner.

In one embodiment, the display 18 may include a touch sensitive layer on the screen that is configured to receive input from the user. In typical embodiments, the touch sensitive layer is configured to recognize a user's touches applied to the surface of the layer. For example, the position of the touches, the pressure of the touches, general direction of the touches, and the like are recognized by the touch sensitive layer. In one embodiment, the functionality of one or more inputs devices can be carried out by icons presented by the touch screen display and activated by an operator's finger, a stylus, etc. In another embodiment, the operator may interact with the virtual keyboard or keypad displayed on the display 18 via a finger, stylus, etc.

The program modules 50, 52, 54, 56, 58, when executed by the computing device 10, may present a graphical user interface to the operator, which may open within a web browser or other graphical environment. The program modules are capable of graphically displaying information to and requesting and/or receiving data from the operator, analyzing data received, and generating canceling, or modifying alerts, notices, warnings, and/or graphical representations of data derived from the passive-alert element. The program modules may further access stored data 14.

Many different arrangements of the various components depicted, as well as components not shown, are possible without departing from the spirit and scope of the disclosed technology. Embodiments of the disclosed technology have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosed technology.

It will be understood that certain features and sub-combinations are of utility and may be employed without reference to other features and sub combinations and are contemplated within the scope of the claims. Not all steps listed in the various figures need be carried out in the specific order described.

We claim:

1. A system for providing user awareness of an aberrant condition within a medical laboratory environment, comprising:

plural subsystems, each for performing analytical testing on biological samples and each having an associated data store for storing functional parameters associated with the respective subsystem; and a computing device comprised of a central processor, a communications interface, an associated display device, and associated data storage, wherein computing device via the associated display device implements a user interface element comprising a graphical representation of conditions associated with at least one of the plural subsystems within the laboratory environment, wherein the communications interface implements a data polling module having pointer parameters referencing data locations within the data store associated with one or more of the plural subsystems for enabling the central processor to selectively retrieve polled data from the data store associated with each of the plural subsystems, wherein the central processor implements a reference module in communication with the data polling module for enabling the central processor to compare retrieved polled data from the respective data locations to respective reference values in the associated data storage, and wherein the central processor further implements an alert module in communication with the reference module for receiving an indication that the comparison of the retrieved polled data to the respective reference values is aberrant and for generating an alert to be displayed by the user interface element in response thereto within the graphical representation.

2. The system of claim 1, wherein the data polling module is further for enabling a user to define the pointer parameters for accessing desired data locations associated with the one or more of the plural subsystems.

3. The system of claim 1, wherein the reference module is further for enabling a user to define the reference values in the associated data storage.

4. The system of claim 1, wherein the alert module is further for enabling a user to define characteristics of the alert.

5. The system of claim 1, wherein the alert module is further for generating the alert as a pop-up window displayed in conjunction with the graphical representation.

6. The system of claim 5, wherein the pop-up window comprises at least the retrieved polled data value and the respective reference value.

7. The system of claim 1, wherein the reference module is configured to retain types of reference values selected from the group consisting of specific data values, data ranges, text strings, regular expressions and element identifiers.

8. The system of claim 1, wherein the data polling module is configured to retrieve polled data from each respective data location according to a respective temporal schedule.

9. The system of claim 1, wherein the alert module is configured to cease generating an alert when the comparison of a subsequently retrieved polled data to the respective reference value is positive.

10. The system of claim 1, wherein the alert module is configured to enable a user to delete a previously generated alert regardless of an aberrant comparison between the retrieved polled data and the respective reference value.

11. The system of claim 1, further comprising a status module in communication with the user interface element for selectively displaying data values associated with one or more of the plural subsystems within the graphical representation of conditions associated with the at least one of the plural subsystems to provide a user with real-time information regarding the one or more of the plural subsystems.

12. The system of claim 1, wherein the retrieved polled data comprises data defining a graphical image displayed on a display associated with a respective one of the plural subsystems.

13. The system of claim 12, wherein the reference values comprise data defining a reference graphical image and wherein the reference module is configured for enabling the central processor, implementing the reference module, to compare the retrieved graphical image data to the respective reference graphical image data.

14. The system of claim 1, wherein the central processor, communications module, and associated display device are components of one of the plural subsystems.

15. A method of enabling user awareness of an aberrant condition within an environment having plural subsystems disposed therein, each subsystems having a respective data store, the method comprising:

providing an alert enabled passive element comprising a central processor, a communications interface, and an associated display device for implementing a user interface;

displaying on the associated display device, within the user interface, a graphical representation of conditions associated with at least one of the plural subsystems within the environment;

selectively retrieving polled data at data locations within the data store associated with at least one of the plural subsystems and referenced by pointer parameters by the central processor implementing a data polling module via the communications interface;

comparing retrieved polled data to respective reference values by the central processor implementing a reference module in communication with the data polling module; and generating an alert for display on the associated display device, within the graphical representation of the user interface, by the central processor implementing an alert module in communication with the reference module in response to receiving an indication that the comparison of the retrieved polled data to the respective reference values is aberrant.

16. The method of claim 15, further comprising a user defining the pointer parameters for referencing desired data locations associated with the one or more of the plural subsystems.

17. The method of claim 15, further comprising a user defining the reference values in the reference module.

18. The method of claim 15, further comprising a user defining characteristics of the alert in the alert module.

19. The method of claim 15, further comprising generating the alert by the alert module as a pop-up window displayed in conjunction with the graphical representation.

20. The method of claim 19, wherein the pop-up window comprises at least the retrieved polled data value and the respective reference value.

21. The method of claim 15, further comprising retaining types of reference values, by the reference module, selected from the group consisting of specific data values, data ranges, text strings, regular expressions and element identifiers.

22. The method of claim 15, wherein selectively receiving comprises selectively retrieving the polled data according to a respective temporal schedule.

23. The method of claim 15, further comprising ceasing generation of an alert when the comparison of subsequently retrieved polled data to the respective reference values is positive.

24. The method of claim 15, wherein the alert module is configured to enable a user to delete a previously generated alert regardless of an aberrant comparison between the retrieved polled data and the respective reference values.

25. The method of claim 15, further comprising selectively displaying data values associated with one or more of the plural subsystems within the graphical representation of conditions associated with at least one of the plural subsystems by the processor implementing a status module in communication with the user interface to provide a user with real-time information regarding the one or more of the plural subsystems.

26. The method of claim 15, wherein the retrieved polled data comprises data defining a graphical image displayed on a display associated with a respective one of the plural subsystems.

27. The method of claim 26, wherein the reference values comprise data defining a reference graphical image and wherein comparing retrieved polled data comprises enabling the central processor, implementing the reference module, to compare the retrieved graphical image data to the respective reference graphical image data.

28. The method of claim 15, wherein providing the alert enabled passive element comprises providing the alert enabled passive element comprised of a central processor, communications module, and associated display device of one of the plural subsystems.

* * * * *